(12) United States Patent
Miyata et al.

(10) Patent No.: US 8,758,269 B2
(45) Date of Patent: Jun. 24, 2014

(54) GUIDEWIRE

(75) Inventors: Naohiko Miyata, Nagoya (JP); Makoto Nishigishi, Nagoya (JP); Hideaki Maki, Nagoya (JP); Tadahiro Koike, Nagoya (JP); Yuuya Kanazawa, Nagoya (JP)

(73) Assignee: Asahi Intecc Co., Ltd., Nagoya-shi (JP)

( * ) Notice: Subject to any disclaimer, the term of this patent is extended or adjusted under 35 U.S.C. 154(b) by 56 days.

(21) Appl. No.: 13/355,183

(22) Filed: Jan. 20, 2012

(65) Prior Publication Data

US 2012/0197159 A1 Aug. 2, 2012

(30) Foreign Application Priority Data

Jan. 28, 2011 (JP) ................................ 2011-015918

(51) Int. Cl.
*A61M 25/09* (2006.01)
(52) U.S. Cl.
CPC ..... *A61M 25/09* (2013.01); *A61M 2025/09175* (2013.01); *A61M 2025/09108* (2013.01); *A61M 2025/09083* (2013.01)
USPC ...................................................... 600/585
(58) Field of Classification Search
CPC .......... A61M 25/09; A61M 25/09016; A61M 25/09025; A61M 25/09033; A61M 25/0905
USPC .................... 600/585, 434; 604/510
See application file for complete search history.

(56) References Cited

U.S. PATENT DOCUMENTS

| | | | | | |
|---|---|---|---|---|---|
| 4,854,330 | A | * | 8/1989 | Evans et al. | 600/585 |
| 5,067,489 | A | * | 11/1991 | Lind | 600/585 |
| 5,069,226 | A | * | 12/1991 | Yamauchi et al. | 600/585 |
| 5,147,317 | A | * | 9/1992 | Shank et al. | 604/164.13 |
| 5,171,383 | A | * | 12/1992 | Sagae et al. | 148/564 |
| 5,184,621 | A | * | 2/1993 | Vogel et al. | 600/381 |
| 5,238,004 | A | * | 8/1993 | Sahatjian et al. | 600/585 |
| 5,353,798 | A | * | 10/1994 | Sieben | 600/462 |
| 5,353,808 | A | * | 10/1994 | Viera | 600/585 |
| 5,354,623 | A | * | 10/1994 | Hall | 428/610 |
| 5,404,887 | A | * | 4/1995 | Prather | 600/585 |
| 5,449,369 | A | * | 9/1995 | Imran | 606/159 |
| 5,480,382 | A | * | 1/1996 | Hammerslag et al. | 604/528 |
| 5,666,969 | A | * | 9/1997 | Urick et al. | 600/585 |
| 5,673,707 | A | * | 10/1997 | Chandrasekaran | 600/585 |

(Continued)

FOREIGN PATENT DOCUMENTS

DE 101 38 953 A1 2/2003
EP 0 410 557 A2 1/1991

(Continued)

OTHER PUBLICATIONS

Extended European Search Report dated May 22, 2012 in corresponding European Patent Application No. EP 12 15 1420.2.

(Continued)

*Primary Examiner* — Sean Dougherty
*Assistant Examiner* — Michael C Stout
(74) *Attorney, Agent, or Firm* — Oliff PLC

(57) ABSTRACT

A guidewire includes a core shaft, and a coiled body wound around the outer circumferential surface of the core shaft. A bulged portion is provided at the tip portion of the core shaft. The front end of the coiled body is bonded to the front end of the core shaft with a bonding portion. The bonding portion is provided to enclose the bulged portion provided at the tip portion of the core shaft.

8 Claims, 6 Drawing Sheets

(56) References Cited

U.S. PATENT DOCUMENTS

| | | | |
|---|---|---|---|
| 5,746,701 A * | 5/1998 | Noone | 600/585 |
| 5,776,080 A * | 7/1998 | Thome et al. | 600/585 |
| 5,788,654 A * | 8/1998 | Schwager | 600/585 |
| 5,797,857 A * | 8/1998 | Obitsu | 600/585 |
| 5,865,767 A * | 2/1999 | Frechette et al. | 600/585 |
| 5,891,055 A * | 4/1999 | Sauter | 600/585 |
| 5,916,178 A * | 6/1999 | Noone et al. | 600/585 |
| 6,004,279 A * | 12/1999 | Crowley et al. | 600/585 |
| 6,500,130 B2 * | 12/2002 | Kinsella et al. | 600/585 |
| 6,592,570 B2 * | 7/2003 | Abrams et al. | 604/525 |
| 6,610,046 B1 * | 8/2003 | Usami et al. | 604/530 |
| 7,494,474 B2 * | 2/2009 | Richardson et al. | 600/585 |
| 7,632,303 B1 * | 12/2009 | Stalker et al. | 623/1.19 |
| 7,699,792 B2 * | 4/2010 | Hofmann et al. | 600/585 |
| 7,753,859 B2 * | 7/2010 | Kinoshita et al. | 600/585 |
| 7,785,274 B2 * | 8/2010 | Mishima et al. | 600/585 |
| 7,883,474 B1 * | 2/2011 | Mirigian et al. | 600/585 |
| 8,021,311 B2 * | 9/2011 | Munoz et al. | 600/585 |
| 8,267,872 B2 * | 9/2012 | Ressemann et al. | 600/585 |
| 8,348,858 B2 * | 1/2013 | Viswanathan et al. | 600/585 |
| 8,348,860 B2 * | 1/2013 | Murayama et al. | 600/585 |
| 8,353,850 B2 * | 1/2013 | Ressemann et al. | 600/585 |
| 8,360,995 B2 * | 1/2013 | Elsesser et al. | 600/585 |
| 2002/0062092 A1 * | 5/2002 | Muni et al. | 600/585 |
| 2002/0082524 A1 * | 6/2002 | Anderson et al. | 600/585 |
| 2002/0087099 A1 * | 7/2002 | Nanis et al. | 600/585 |
| 2003/0102360 A1 * | 6/2003 | Eungard et al. | 228/224 |
| 2003/0120181 A1 * | 6/2003 | Toma et al. | 600/585 |
| 2003/0125642 A1 * | 7/2003 | Kato et al. | 600/585 |
| 2004/0111044 A1 * | 6/2004 | Davis et al. | 600/585 |
| 2004/0167436 A1 * | 8/2004 | Reynolds et al. | 600/585 |
| 2004/0167442 A1 * | 8/2004 | Shireman et al. | 600/585 |
| 2004/0181175 A1 * | 9/2004 | Clayman et al. | 600/585 |
| 2004/0225231 A1 * | 11/2004 | Ehr | 600/585 |
| 2004/0243168 A1 * | 12/2004 | Ferrera et al. | 606/191 |
| 2005/0096568 A1 * | 5/2005 | Kato | 600/585 |
| 2005/0137501 A1 * | 6/2005 | Euteneuer et al. | 600/585 |
| 2005/0145307 A1 * | 7/2005 | Shireman et al. | 148/565 |
| 2005/0267385 A1 * | 12/2005 | Hofmann et al. | 600/585 |
| 2005/0273021 A1 * | 12/2005 | Burgermeister | 600/585 |
| 2006/0122537 A1 * | 6/2006 | Reynolds et al. | 600/585 |
| 2006/0241519 A1 * | 10/2006 | Hojeibane et al. | 600/585 |
| 2006/0264784 A1 * | 11/2006 | Lupton | 600/585 |
| 2006/0272751 A1 * | 12/2006 | Kato | 148/540 |
| 2007/0123805 A1 * | 5/2007 | Shireman et al. | 600/585 |
| 2007/0185415 A1 * | 8/2007 | Ressemann et al. | 600/585 |
| 2007/0198044 A1 * | 8/2007 | Lupton et al. | 606/191 |
| 2007/0219464 A1 * | 9/2007 | Davis et al. | 600/585 |
| 2007/0219465 A1 * | 9/2007 | Cedro et al. | 600/585 |
| 2007/0244413 A1 * | 10/2007 | Biggins | 600/585 |
| 2007/0249965 A1 * | 10/2007 | Abrams et al. | 600/585 |
| 2008/0004546 A1 * | 1/2008 | Kato | 600/585 |
| 2008/0097248 A1 * | 4/2008 | Munoz et al. | 600/585 |
| 2008/0161726 A1 * | 7/2008 | Itou | 600/585 |
| 2008/0200879 A1 * | 8/2008 | Jalisi et al. | 604/164.13 |
| 2008/0228109 A1 * | 9/2008 | Kinoshita et al. | 600/585 |
| 2008/0234605 A1 * | 9/2008 | Urie | 600/585 |
| 2008/0281230 A1 * | 11/2008 | Kinoshita et al. | 600/585 |
| 2008/0306453 A1 | 12/2008 | Elsesser et al. | |
| 2009/0000105 A1 * | 1/2009 | Kato | 29/428 |
| 2009/0163833 A1 * | 6/2009 | Kinoshita et al. | 600/585 |
| 2009/0318835 A1 * | 12/2009 | Ressemann et al. | 600/585 |
| 2010/0004562 A1 * | 1/2010 | Jalisi et al. | 600/585 |
| 2010/0158436 A1 * | 6/2010 | Riska | 385/14 |
| 2010/0249654 A1 * | 9/2010 | Elsesser et al. | 600/585 |
| 2010/0318065 A1 | 12/2010 | Miyata et al. | |
| 2011/0319872 A1 * | 12/2011 | Kawasaki | 604/528 |
| 2012/0109108 A1 * | 5/2012 | Boyle et al. | 604/528 |
| 2013/0006149 A1 * | 1/2013 | Purtzer | 600/585 |
| 2013/0006222 A1 * | 1/2013 | Nabeshima et al. | 604/528 |

FOREIGN PATENT DOCUMENTS

| | | |
|---|---|---|
| EP | 0 818 215 A1 | 1/1998 |
| JP | Y-S13-8111 | 6/1938 |
| JP | U-S55-22573 | 2/1980 |
| JP | A-5-256310 | 10/1993 |
| JP | U-06-081547 | 11/1994 |
| JP | B2-2990199 | 10/1999 |
| JP | A-2003-52829 | 2/2003 |
| JP | A-2010-214054 | 9/2010 |
| JP | A-2011-00188 | 1/2011 |
| WO | WO 90/01892 | 3/1990 |
| WO | WO 90/01892 A1 | 3/1990 |
| WO | WO 02/32344 A2 | 4/2002 |

OTHER PUBLICATIONS

Jan. 16, 2013 Office Action issued in Japanese Patent Application No. 2011-015918 (with translation).

Chinese Office Action issued in Chinese Patent Application No. 201210018038.2 dated Feb. 7, 2014 (w/ translation).

* cited by examiner

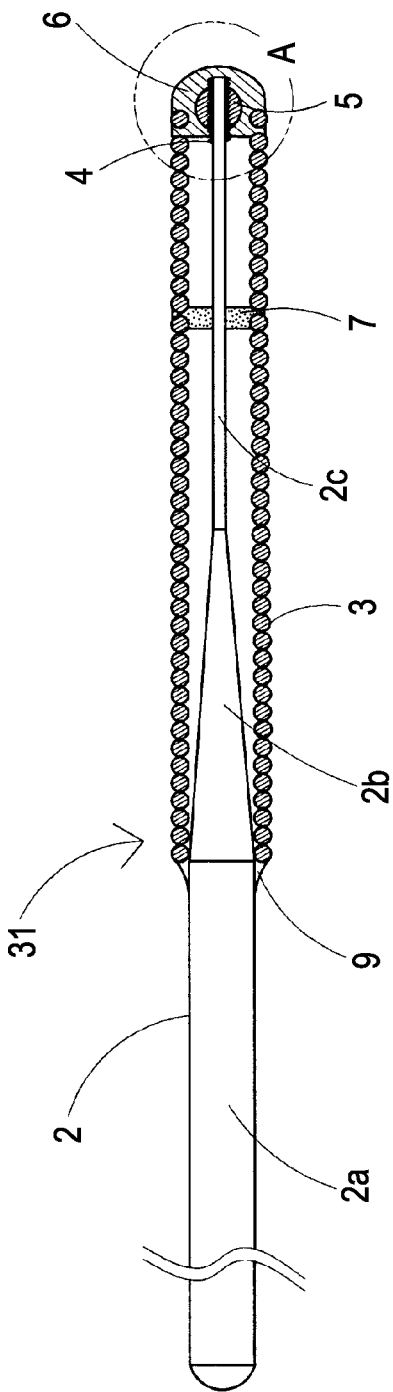

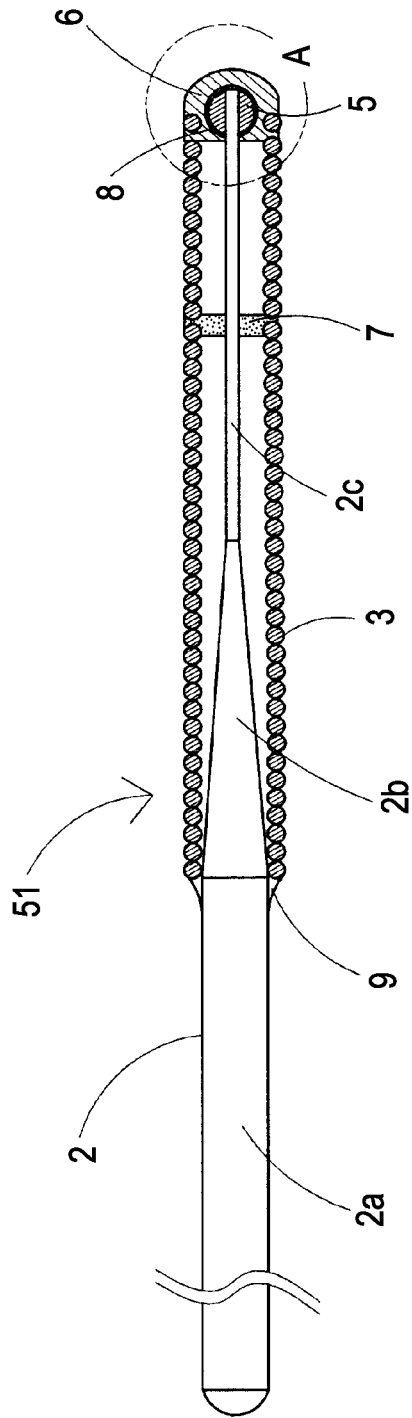
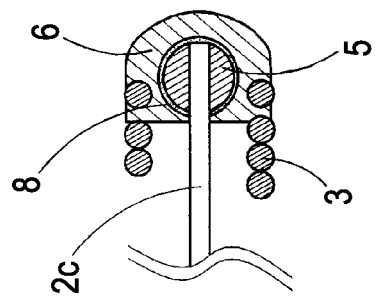

GUIDEWIRE

CROSS-REFERENCE TO RELATED APPLICATION

This application claims priority to Japanese Patent Application No. 2011-015918 filed with the Japan Patent Office on Jan. 28, 2011, the entire contents of which are hereby incorporated by reference.

The disclosed embodiments relate to a medical device. More specifically, the disclosed embodiments relate to a guidewire.

BACKGROUND

In the related art, various types of guidewires have been proposed which are used for guiding, for example, a medical device to a target site by being inserted into a tubular organ such as a vessel, a digestive tract, and an ureter, or an intracorporeal tissue.

In the guidewire described in, for example, JP-UM-A-6-81547, a head portion is provided at a front end of a core, and is bonded to a front end of a coil with brazing metal.

In the guidewire described in JP-A-2010-214054, a core wire is bonded to a front end of a coil spring with Au—Sn-based solder. Also, resin is filled inside this guidewire.

SUMMARY

In the guidewire described in JP-UM-A-6-81547, however, the head portion is only partially coated with the brazing metal used for bonding the head portion to the coil. Therefore, the bonding strength is not enough. As a result, the front end of the coil may come off from the core wire, in which case the detached coil tends to damage the inside of, or remain inside, a vascular channel such as a vessel.

In the guidewire described in JP-A-2010-214054, the core wire is bonded to the front end of the coil spring with Au—Sn-based solder. With this configuration, the bonding strength is somewhat higher. Since the tip portion of the core wire is bonded to the coil spring, however, the resin-filled inside the guidewire does not make the bonding strength enough to prevent detachment. As with the guidewire described in JP-UM-A-6-81547, therefore, the front end of the coil spring may come off from the core wire, and the coil spring tends to damage the inside of, or remain inside, a vascular channel such as a vessel.

The disclosed embodiments have been made in view of the above circumstances. An object of the disclosed embodiments is to provide a guidewire with improved safety, by increasing the bonding strength between a core shaft of the guidewire and a coiled body.

A guidewire according to a first aspect of the present invention includes: a core shaft; a coiled body covering the core shaft; a bulged portion formed at a tip portion of the core shaft; and a bonding portion for bonding a front end of the coiled body to a front end of the core shaft, the bonding portion being provided to enclose the bulged portion.

BRIEF DESCRIPTION OF THE DRAWINGS

The foregoing and other objects, features, aspects and advantages of the disclosed embodiments will become more apparent from the following detailed description when taken in conjunction with the accompanying drawings.

FIGS. 4A and 4B are views each illustrating the configuration of a guidewire according to a fourth embodiment of the present invention, wherein FIG. 4A is a view illustrating the entire guidewire, and FIG. 4B is a partially enlarged view of the guidewire;

FIGS. 5A to 5E are views each illustrating the configuration of a guidewire according to a fifth embodiment of the present invention, wherein FIG. 5A is a view illustrating the entire guidewire, FIG. 5B is an enlarged view of the A-A section in FIG. 5A, FIG. 5C is an enlarged view of the B-B section in FIG. 5A, and FIGS. 5D and 5E are enlarged views of the B-B section in FIG. 5A according to modifications; and FIGS. 6A and 6B are views each illustrating the configuration of a guidewire according to a sixth embodiment of the present invention, wherein FIG. 6A is a view illustrating the entire guidewire, and FIG. 6B is a partially enlarged view of the guidewire.

DETAILED DESCRIPTION OF EMBODIMENTS

Figure 1:
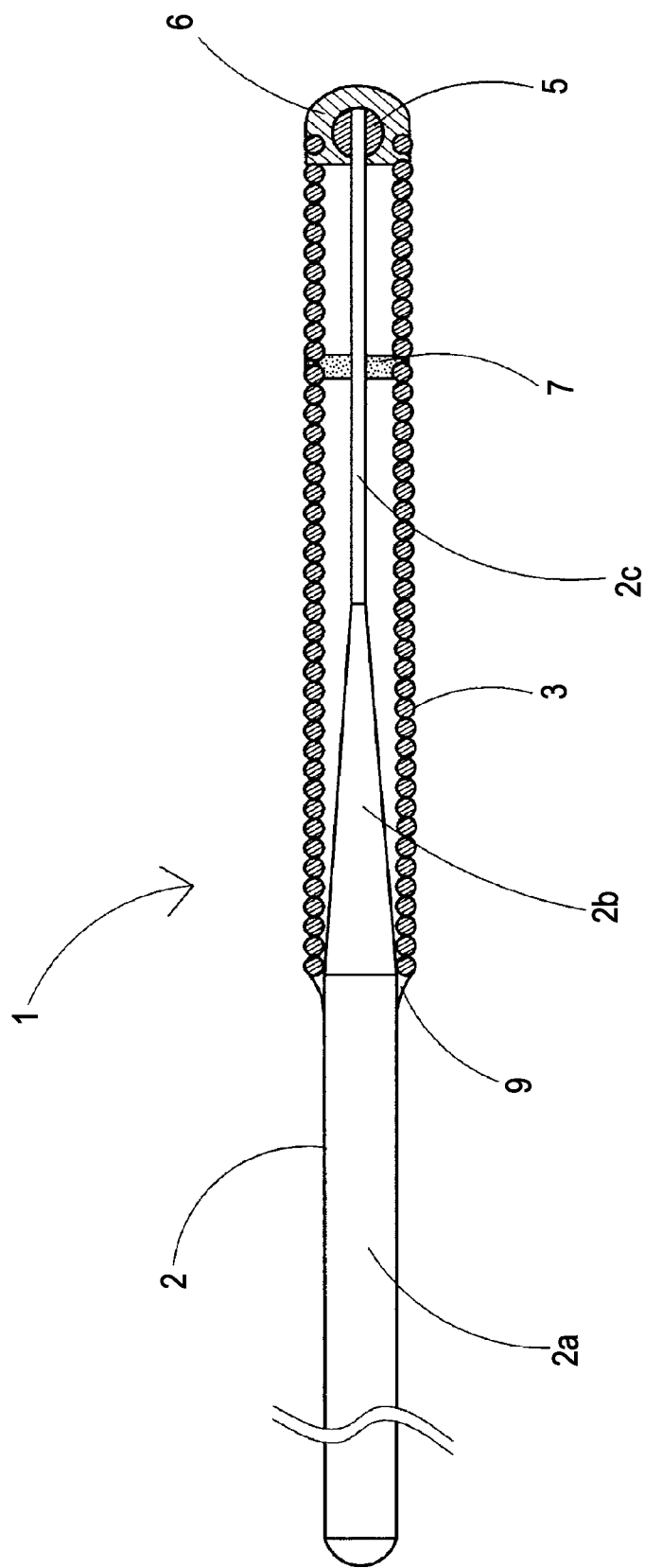
FIG. 1 is a view illustrating an entire guidewire according to a first embodiment of the present invention.

Preferred embodiments of a present invention are described below with reference to the accompanying drawings, in which like reference characters designate similar or identical parts throughout the several views thereof.

A guidewire according to the first aspect of the present invention includes: a core shaft; a coiled body covering the core shaft; a bulged portion formed at a tip portion of the core shaft; and a bonding portion for bonding a front end of the coiled body to a front end of the core shaft, the bonding portion being provided to enclose the bulged portion.

A second aspect of the present invention is the guidewire according to the first aspect, wherein a material constituting the bulged portion has a higher stiffness than a material constituting the bonding portion.

A third aspect of the present invention is the guidewire according to the first or second aspect, wherein a material constituting the bulged portion is a first metal solder, and a material constituting the bonding portion is a second metal solder having a lower melting point than the first metal solder.

A fourth aspect of the present invention is the guidewire according to the third aspect, wherein the first metal solder contains 80 wt % or more gold component.

A fifth aspect of the present invention is the guidewire according to any one of the first to fourth aspects, wherein the bulged portion has an outer diameter larger than an inner diameter of the coiled body.

A sixth aspect of the present invention is the guidewire according to any one of the first to fifth aspects, further including: an inner coiled body positioned inside the coiled body, wherein a front end of the inner coiled body is bonded to the core shaft through the bulged portion, and a proximal end of the inner coiled body is bonded to the core shaft between the front end of the inner coiled body and a proximal end of the coiled body.

A seventh aspect of the present invention is the guidewire according to any one of the first to sixth aspects, wherein a concavo-convex engaging portion is provided at the tip portion of the core shaft, and at least one of the bulged portion and the bonding portion is positioned on the engaging portion.

An eighth aspect of the present invention is the guidewire according to any one of the first to seventh aspects, wherein a flattened portion having a flattened cross-section is provided at the tip portion of the core shaft, at least one of the width and thickness of the flattened portion increases toward a front end thereof, and the bulged portion is formed at the flattened portion.

In the guidewire according to the first aspect, the bulged portion is formed at the tip portion of the core shaft. The front end of the core shaft is bonded to the front end of the coiled body with the bonding portion provided to enclose the bulged portion. This configuration increases the bonding strength between the front end of the coiled body and the front end of the core shaft. Therefore, it is possible to prevent the bonding portion from coming off from the tip portion of the core shaft even when the tensile load or compressive load is applied to the front end of the coiled body. As a result, the safety of the guidewire can be improved.

In the guidewire according to the second aspect, the material for the bulged portion has a higher stiffness than the material for the bonding portion. This makes it difficult to deform the bulged portion. Therefore, the bonding strength between the front end of the coiled body and the front end of the core shaft can be further increased. It is thus possible to further reliably prevent the coiled body of the guidewire from coming off from the core shaft. As a result, the safety of the guidewire can be further improved.

In the guidewire according to the third aspect, the material for the bulged portion is the first metal solder. In addition, the material for the bonding portion is the second metal solder having a lower melting point than the first metal solder. This makes it possible to suppress the thermal impact, caused by the second metal solder, on the core shaft and the coiled body, and to firmly bond the front end of the core shaft to the front end of the coiled body. It is thus possible to further reliably prevent the coiled body of the guidewire from coming off from the core shaft. As a result, the safety of the guidewire can be further improved.

In the guidewire according to the fourth aspect, the first metal solder used to form the bulged portion contains 80 wt % or more gold component. Therefore, the guidewire according to the fourth aspect has the advantages of the guidewire according to the third aspect and, in the former guidewire, the front end of the core shaft can be more firmly bonded to the front end of the coiled body. It is thus possible to further reliably prevent the coiled body of the guidewire from coming off from the core shaft. As a result, the safety of the guidewire can be further improved.

Furthermore, the metal solder containing 80 wt % or more gold component is also highly radiopaque. Therefore, the front end of the guidewire is clearly imaged by the imaging under radioscopy. This allows an operator to visually locate the guidewire easily, which in turn allows the operator to manipulate the guidewire safely.

In the guidewire according to the fifth aspect, the outer diameter of the bulged portion is larger than the inner diameter of the coiled body. Therefore, it is possible to reliably prevent the coiled body from coming off from the core shaft. As a result, the safety of the guidewire can be significantly improved.

The guidewire according to the sixth aspect further includes the inner coiled body positioned inside the coiled body. The front end of the inner coiled body is bonded to the core shaft through the bulged portion. The proximal end of the inner coiled body is bonded to the core shaft between the front end of the inner coiled body and the proximal end of the coiled body. With this configuration, the tensile load or compressive load applied to the bulged portion can be distributed among the core shaft, the coiled body, and the inner coiled body. It is thus possible to further reliably prevent the bulged portion and the bonding portion from coming off from the core shaft. As a result, the safety of the guidewire can be further improved.

The guidewire according to the seventh aspect includes the concavo-convex engaging portion at the tip portion of the core shaft. The material for the bulged portion and/or the bonding portion is flowed into the engaging portion. Therefore, the bonding strength between the front end of the core shaft and the front end of the coiled body can be significantly increased. It is thus possible to further reliably prevent the coiled body from coming off from the core shaft. As a result, the safety of the guidewire can be significantly improved.

The guidewire according to the eighth aspect includes the flattened portion, having a flattened cross-section, at the tip portion of the core shaft. The width and/or thickness of the flattened portion increase toward the front end thereof. Furthermore, the bulged portion is formed at the flattened portion. Therefore, the bonding strength between the front end of the core shaft and the front end of the coiled body can be significantly increased. It is thus possible to reliably prevent the coiled body from coming off from the core shaft. As a result, the safety of the guidewire can be significantly improved.

Guidewires according to preferred embodiments of the present invention will be described below with reference to the drawings.

FIG. 1 is a view illustrating the entire guidewire according to a first embodiment of the present invention.

Note that, for the sake of description, the left side in FIG. 1 is a proximal end, while the right side is a front end.

FIG. 1 illustrates an entire guidewire 1 schematically with its length reduced for easy understanding. Therefore, the dimensional ratio of the entire guidewire illustrated is different from the dimensional ratio of the actual guidewire.

As illustrated in FIG. 1, the guidewire 1 includes a core shaft 2, and a coiled body 3 covering a tip portion of the core shaft 2.

The core shaft 2 includes a large-diameter portion 2a, a tapered portion 2b, and a small-diameter portion 2c. The tapered portion 2b is arranged at the front end of the large-diameter portion 2a. The outer diameter of the tapered portion 2b decreases toward the front end thereof. The small-diameter portion 2c is arranged at the front end of the tapered portion 2b.

A bulged portion 5 is formed at the tip portion of the small-diameter portion 2c of the core shaft 2. The front end of the small-diameter portion 2c of the core shaft 2 is bonded to the front end of the coiled body 3 with a bonding portion 6. The bonding portion 6 is provided to enclose the bulged portion 5.

The front end of the large-diameter portion 2a of the core shaft 2 is bonded to the proximal end of the coiled body 3 with a proximal end bonding portion 9.

A middle portion of the small-diameter portion 2c of the core shaft 2 is bonded to a middle portion of the coiled body 3 with a middle bonding portion 7.

In this manner, the guidewire 1 has the bulged portion 5 formed at the tip portion of the small-diameter portion 2c of the core shaft 2. The front end of the small-diameter portion 2c of the core shaft 2 is bonded to the front end of the coiled body 3 with the bonding portion 6 provided to enclose the bulged portion 5. In this manner, the bulged portion 5 of the guidewire 1 can enhance the bonding strength between the front end of the coiled body 3 and the front end of the small-diameter portion 2c of the core shaft 2. This configuration can prevent the coiled body 3 of the guidewire 1 from coming off from the small-diameter portion 2c of the core shaft 2 even when a tensile load or compressive load is applied to the front end of the coiled body 3. As a result, the safety of the guidewire 1 can be improved.

Next, materials constituting the guidewire 1 according to the first embodiment will be described.

Examples of the material for the core shaft 2 include, but are not limited to, stainless steel (SUS304), super elastic alloys such as an Ni—Ti alloy, and piano wire.

Examples of the material for the coiled body 3 include a radiopaque strand and a radiolucent strand.

Examples of the material for the radiopaque strand include, but are not limited to, gold, platinum, tungsten, and an alloy containing these elements (e.g., platinum-nickel alloy).

Examples of the material for the radiolucent strand include, but are not limited to, stainless steel (e.g., SUS304 and SUS316), super elastic alloys such as an Ni—Ti alloy, and piano wire.

The coiled body 3 may be formed to include the radiopaque strand and the radiolucent strand. In this case, for example, the front side of the middle bonding portion 7 of the coiled body 3 can be formed of the radiopaque strand, and the proximal side of the middle bonding portion 7 in the coiled body 3 can be formed of the radiolucent strand. The radiopaque strand and the radiolucent strand may be bonded to each other with endfaces thereof abutting against, and welded to, each other. Both strands may be bonded to each other by covering the abutting portions of both strands with the middle bonding portion 7.

This improves the visibility, under radioscopy, of the front side of the middle bonding portion 7 in the coiled body 3. This allows an operator to easily locate the tip portion of the guidewire 1. As a result, the operator can manipulate the guidewire 1 safely.

The bulged portion 5 can be formed by fusing the front end of the small-diameter portion 2c of the core shaft 2 by using a plasma welder or TIG welder. The bulged portion 5 can also be formed by several windings of a metal thin wire around the tip portion of the small-diameter portion 2c of the core shaft 2, and fusing the wound metal thin wire with the front end of the small-diameter portion 2c of the core shaft 2 by using the above method. When a radiopaque metal thin wire is used as the metal thin wire to be wound around the tip portion of the small-diameter portion 2c of the core shaft 2, the radiopaque bulged portion 5 can be formed at the tip portion of the small-diameter portion 2c of the core shaft 2. Therefore, the visibility of the guidewire 1 under radioscopy can be improved.

Alternatively, the bulged portion 5 can also be formed by using a resin material. Examples of the resin material include, but are not limited to, synthetic resins, which include, but are not limited to, various elastomer materials such as polysulfone, polyurethane, polyamide, polyimide, or polyether ether ketone, and an adhesive such as epoxy resin. When forming the bulged portion 5 from such a resin material, it is preferable that the tip portion of the small-diameter portion 2c of the core shaft 2 be subjected to, for example, surface reforming by irradiation of plasma or ultraviolet ray, degreasing wash, or priming. This can enhance the bonding strength between the core shaft 2 and the resin material constituting the bulged portion 5.

Note that the resin member constituting the bulged portion 5 is bonded (applied) to the tip portion of the small-diameter portion 2c of the core shaft 2 through, for example, reaction of molten resin, resin dissolved in a solvent, or a resin precursor such as monomer and reactive compound.

A first metal solder (e.g., brazing material and solder) is preferably used as the material for the bulged portion 5. The use of the first metal solder makes it possible to easily form the bulged portion 5 while maintaining the bonding strength of the bulged portion 5 with respect to the small-diameter portion 2c of the core shaft 2.

Examples of the material for the first metal solder include, but are not limited to, aluminum alloy solder, silver solder, gold solder, zinc, Sn—Pb alloy, Pb—Ag alloy, Sn—Ag alloy, Au—Sn alloy, and Au—Si alloy. Among these, the preferred material for the first metal solder is a metal solder such as gold solder, Au—Sn alloy, and Au—Si alloy which are metal solders containing 80 wt % or more gold component. The metal solder containing 80 wt % or more gold component has a high stiffness. Therefore, by using this metal solder, the front end of the small-diameter portion 2c of the core shaft 2 can be more firmly bonded to the front end of the coiled body 3. It is thus possible to more reliably prevent the coiled body 3 of the guidewire 1 from coming off from the small-diameter portion 2c of the core shaft 2. As a result, the safety of the guidewire 1 can be further improved.

The metal solder containing 80 wt % or more gold component is also highly radiopaque. Therefore, the front end of the guidewire 1 is clearly imaged by the imaging under radioscopy. This allows the operator to visually locate the guidewire 1 easily, which in turn allows the operator to manipulate the guidewire 1 safely.

When the bulged portion 5 is formed at the small-diameter portion 2c of the core shaft 2 using the first metal solder, flux may be applied in advance to a part of the small-diameter portion 2c of the core shaft 2 where the bulged portion 5 is to be formed. With this treatment, the bonding strength between the bulged portion 5 formed of the metal solder and the core shaft 2 can be increased.

Examples of the material for the bonding portion 6 include a resin member and a second metal solder.

Examples of the resin member constituting the bonding portion 6 may include, but are not limited to, the above-mentioned resin member constituting the bulged portion 5. In the case where the bulged portion 5 is formed of the metal solder, an adhesive such as epoxy resin is preferably used as the material for the bonding portion 6. The adhesive is capable of bonding thereto various materials as well as resin materials and metal materials. Therefore, the small-diameter portion 2c of the core shaft 2, having the bulged portion 5 formed of the metal solder, can be bonded to the coiled body 3 with the bonding strength maintained.

Examples of the material for the second metal solder constituting the bonding portion 6 include, but are not limited to, the above-mentioned material for the first metal solder constituting the bulged portion 5.

The material for the bulged portion 5 preferably has a higher stiffness than the material for the bonding portion 6. In this case, the bulged portion 5 is formed from the material having a higher stiffness than the material for the bonding portion 6. This makes it difficult to deform the bulged portion 5. Therefore, the bonding strength between the front end of the small-diameter portion 2c of the core shaft 2 and the front end of the coiled body 3 can be further increased. It is thus possible to more reliably prevent the coiled body 3 of the guidewire 1 from coming off from the core shaft 2. As a result, the safety of the guidewire 1 can be further improved.

Examples of the combination of the material for the bonding portion 6 and the material with a higher stiffness for the bulged portion 5 include the combination of polyamide (material for the bulged portion 5) and polyamide elastomer as a kind of elastomers (material for the bonding portion 6), the combination of a metal solder (material for the bulged portion 5) and an adhesive such as epoxy resin (material for the bonding portion 6), and the combination of Au—Sn alloy (material for the bulged portion 5) and Sn—Ag alloy (material for the bonding portion 6). However, the material for the bulged portion 5 is not limited to the above examples, as long as it has a higher stiffness than the material for the bonding portion 6.

In the case where the bulged portion 5 is formed of the first metal solder and the bonding portion 6 is formed of the second metal solder, the second metal solder preferably has a lower melting point than the first metal solder. In this case, it is possible to form the bonding portion 6 while preventing the deformation of the bulged portion 5. Also in this case, the bulged portion 5 is formed of the first metal solder and the bonding portion 6 is formed of the second metal solder having a lower melting point than the first metal solder. Therefore, it is possible to suppress the thermal impact, caused by the second metal solder, on the small-diameter portion 2c of the core shaft 2 and the coiled body 3, and to firmly bond the front end of the small-diameter portion 2c of the core shaft 2 to the front end of the coiled body 3. It is thus possible to further reliably prevent the coiled body 3 of the guidewire 1 from coming off from the core shaft 2. As a result, the safety of the guidewire 1 can be further improved.

Examples of the combination of the first metal solder constituting the bulged portion 5 and the second metal solder having a lower melting point than the first metal solder and constituting the bonding portion 6 include the combination of Au—Sn alloy (first metal solder) and Sn—Ag alloy (second metal solder). However, the second metal solder is not limited to the above example, as long as it has a lower melting point than the first metal solder.

To form the bonding portion 6 from the second metal solder, flux is preferably applied in advance to the small-diameter portion 2c of the core shaft 2 and the portion of the coiled body 3 where the bonding portion 6 is to be formed. In this case, the bonding strength between the front end of the small-diameter portion 2c of the core shaft 2 and the front end of the coiled body 3 can be increased.

The materials for the proximal end bonding portion 9 bonding the front end of the large-diameter portion 2a of the core shaft 2 to the proximal end of the coiled body 3, and for the middle bonding portion 7 bonding the middle portion of the small-diameter portion 2c of the core shaft 2 to the middle portion of the coiled body 3 are not particularly limited. Examples of the material for the proximal end bonding portion 9 and the middle bonding portion 7 include a metal solder such as aluminum alloy solder, silver solder, gold solder, zinc, Sn—Pb alloy, Pb—Ag alloy, Sn—Ag alloy, Au—Sn alloy and Au—Si alloy, and synthetic resin such as various elastomer materials (e.g., polyethylene, polypropylene, and polyamide) and an adhesive (e.g., epoxy resin).

To bond a plurality of members to one another with a metal solder, flux is preferably applied to bonding positions of the members. This improves the wettability between the metal solder and the members. Therefore, the bonding strength between the members is increased.

When the core shaft 2 and the coiled body 3 are bonded to each other with the bonding portion 6, the middle bonding portion 7, and the proximal end bonding portion 9, a gap may be formed in advance between coil strands at the positions of the coiled body 3 where the bonding portion 6, the middle bonding portion 7, and the proximal end bonding portion 9 are to be formed. In this case, the resin member or metal solder enters the gap. As a result, the bonding strength between the core shaft 2 and the coiled body 3 can be increased.

Although not illustrated, the entire circumferential surface of the guidewire 1 or a part of its length may be coated with resin and hydrophobic or hydrophilic lubricant. When the guidewire 1 is coated in this manner, it is preferable to coat the guidewire 1 with resin and to further coat the resin with hydrophilic lubricant so as to cover the entire surfaces of the bonding portion 6 and the coiled body 3 (the entire circumferential surfaces including the long- and short-axis directions thereof).

By coating the entire circumferential surfaces of the bonding portion 6 and the coiled body 3 with resin in this manner, the bonding strength between the coiled body 3 and the hydrophilic lubricant, and the durability of the hydrophilic lubricant can be enhanced. By further coating the resin with the hydrophilic lubricant, the friction between a stenosis inside a vessel and the bonding portion 6 or the coiled body 3 can be reduced, even when the bonding portion 6 or the coiled body 3 comes into contact with the stenosis. This can significantly reduce the possibility of the bonding portion 6 or the coiled body 3 being caught in the stenosis. This also significantly reduces tensile stress or compressive stress, applied to the bulged portion 5 and the bonding portion 6, caused by the operation of pushing and pulling the guidewire 1 when the guidewire 1 is caught in the stenosis. Therefore, the core shaft 2 and the coiled body 3 can be kept bonded to each other. As a result, the safety of the guidewire 1 can be improved.

The guidewire 1 according to the present embodiment can be manufactured by the following method.

First, a coil strand constituting the coiled body 3 is wound around a mandrel for manufacturing the coiled body. In this manner, the coiled body 3 is formed on the outer circumferential surface of the mandrel. Then, the mandrel is pulled out to complete the coiled body 3.

Note that, after the strand constituting the coiled body 3 is wound around the mandrel for manufacturing the coiled body, the strand may be thermally treated to keep the shape of the coiled body 3. This can alleviate the stress caused when the strand of the coiled body 3 is wound around the mandrel for manufacturing the coiled body.

Next, the large-diameter portion 2a, the tapered portion 2b, and the small-diameter portion 2c are formed at the core shaft 2 by grinding the core shaft 2 using, for example, a centerless grinding machine.

Then, the front end of the small-diameter portion 2c of the core shaft 2 is inserted into the proximal side of the coiled body 3. The coiled body 3 is arranged such that, by the insertion, the front end of the small-diameter portion 2c of the core shaft 2 is positioned on the front side of the front end of the coiled body 3.

Next, flux is applied to the tip portion of the small-diameter portion 2c of the core shaft 2. Then, the first metal solder is brought into contact with the tip portion, applied with the flux, of the small-diameter portion 2c of the core shaft 2 by using a soldering iron. As a result, the bulged portion 5 is formed.

The coiled body 3 is then moved toward the front end thereof. Flux is applied to the proximal end of the coiled body 3 and the front end of the large-diameter portion 2a of the core shaft 2. The proximal end of the coiled body 3 is bonded to the front end of the large-diameter portion 2a of the core shaft 2 with the proximal end bonding portion 9 formed of a metal solder.

Next, flux is applied to the middle portion of the coiled body 3. Then, the middle portion of the small-diameter portion 2c of the core shaft 2 is bonded to the middle portion of the coiled body 3 with the middle bonding portion 7 formed of a metal solder.

Finally, flux is applied to the front end of the small-diameter portion 2c of the core shaft 2 where the bulged portion 5 is formed, and the front end of the coiled body 3. After that, the front end of the small-diameter portion 2c of the core shaft 2 is bonded to the front end of the coiled body 3 by using the soldering iron so that the second metal solder encloses the bulged portion 5. As a result, the bonding portion 6 is formed. With the above steps, the guidewire 1 is manufactured.

Note that, when the bulged portion 5 is smaller than the inner diameter of the coiled body 3, the bulged portion 5 may be formed before the core shaft 2 is inserted into the coiled body 3.

In FIG. 1, the endface of the front end of the small-diameter portion 2c of the core shaft 2 matches the front end of the bulged portion 5. Alternatively, however, the bulged portion 5 may be provided to cover the endface of the front end of the small-diameter portion 2c of the core shaft 2. Further alternatively, the bulged portion 5 may be provided while being shifted toward the proximal end from the endface of the front end of the small-diameter portion 2c of the core shaft 2.

Figure 2:
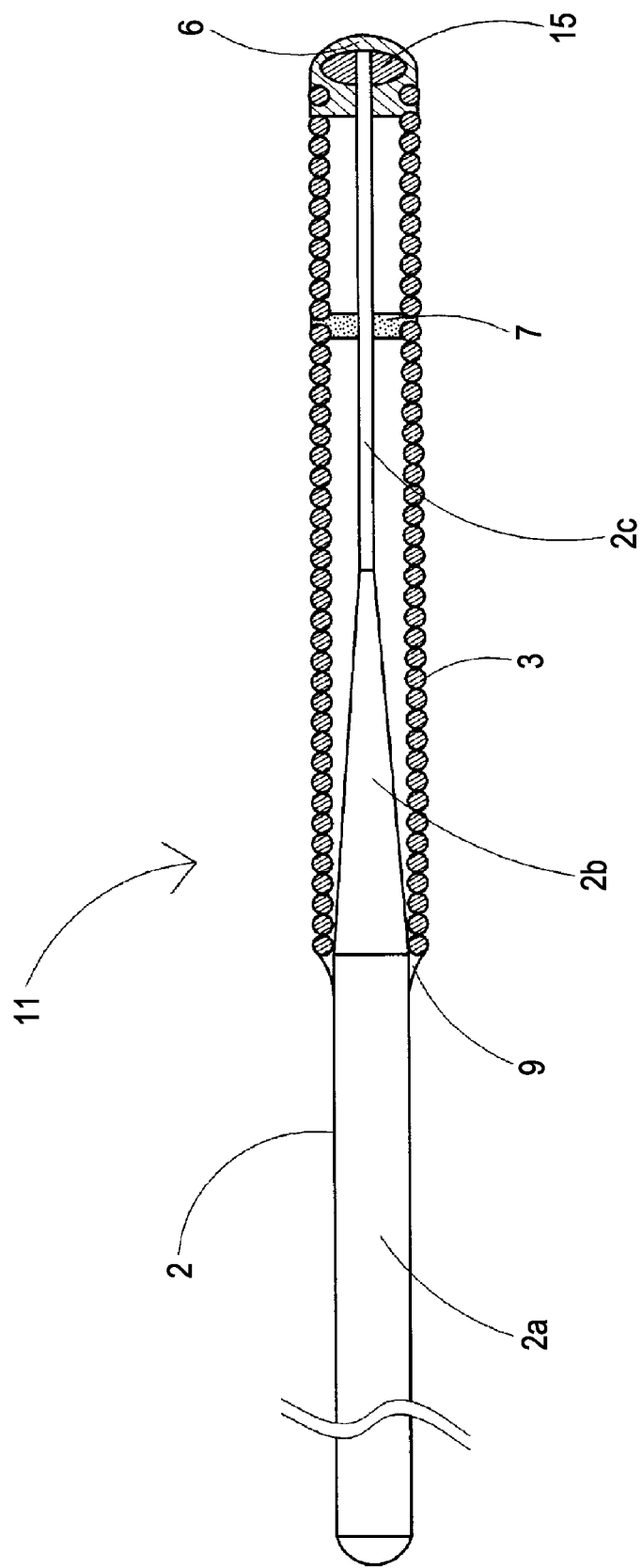
FIG. 2 is a view illustrating an entire guidewire according to a second embodiment of the present invention.

Next, a guidewire 11 according to a second embodiment will be described with reference to FIG. 2, mainly focusing on the difference from the guidewire 1. In FIG. 2, the same portions as those of the guidewire 1 are denoted with the same reference symbols.

For easy understanding, FIG. 2 illustrates the entire guidewire 11 schematically with its length reduced. Therefore, the dimensional ratio of the entire guidewire illustrated is different from the dimensional ratio of the actual guidewire.

Basically, as illustrated in FIG. 2, the guidewire 11 has the same configuration as the guidewire 1. The guidewire 11 is different from the guidewire 1 in that the outer diameter of a bulged portion 15 is larger than the inner diameter of a coiled body 3.

As described, in the guidewire 11, the outer diameter of the bulged portion 15 is larger than the inner diameter of the coiled body 3. It is thus possible to reliably prevent the coiled body 3 from coming off from a core shaft 2. As a result, the safety of the guidewire can be significantly improved.

The guidewire 11 described above can be manufactured in the same manner as the guidewire 1.

In FIG. 2, the longitudinal section of the bulged portion 15 has an elliptical shape elongated in the radial direction of the guidewire 11. However, the shape of the bulged portion 15 is not limited to this example. The bulged portion 15 may have any shape as long as the outer diameter thereof is larger than the inner diameter of the coiled body 3 and the front end of the small-diameter portion 2c of the core shaft 2 is bonded to the front end of the coiled body 3 such that the bonding portion 6 encloses the bulged portion 15.

Figure 3:
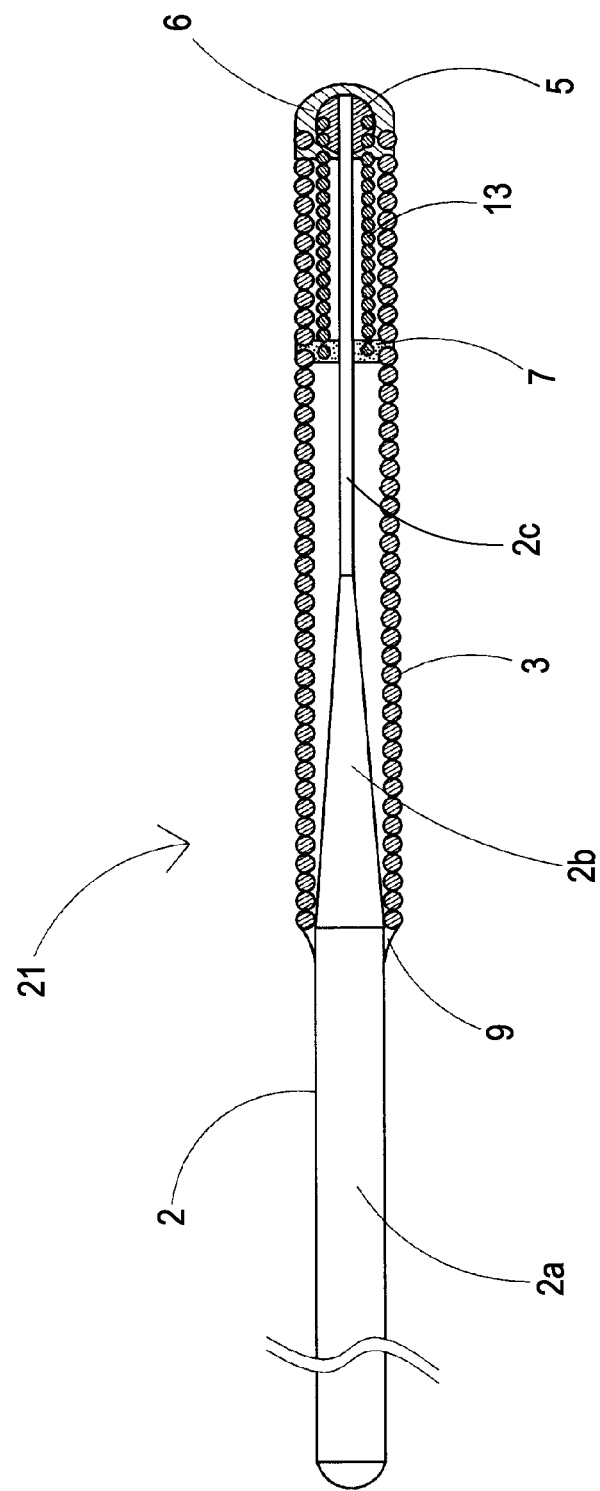
FIG. 3 is a view illustrating an entire guidewire according to a third embodiment of the present invention.

Next, a guidewire 21 according to a third embodiment will be described with reference to FIG. 3, mainly focusing on the difference from the guidewire 1. In FIG. 3, the same portions as those of the guidewire 1 are denoted with the same reference symbols.

For easy understanding, FIG. 3 illustrates the entire guidewire 21 schematically with its length reduced. Therefore, the dimensional ratio of the entire guidewire illustrated is different from the dimensional ratio of the actual guidewire.

As illustrated in FIG. 3, the guidewire 21 includes a core shaft 2, a coiled body 3 covering a tip portion of the core shaft 2, and an inner coiled body 13 positioned inside the coiled body 3. The front end of the inner coiled body 13 is bonded to the front end of a small-diameter portion 2c of the core shaft 2 with a bulged portion 5. The proximal end of the inner coiled body 13 is bonded to a middle portion of the small-diameter portion 2c of the core shaft 2 and a middle portion of the coiled body 3 through a middle bonding portion 7. The front end of the coiled body 3 is bonded to the front end of the core shaft 2 and the front end of the inner coiled body 13 with the bonding portion 6. The bonding portion 6 is provided to enclose the bulged portion 5. The proximal end of the coiled body 3 is bonded to the front end of the large-diameter portion 2a of the core shaft 2 with the proximal end bonding portion 9.

As described above, the guidewire 21 further includes the inner coiled body 13 positioned inside the coiled body 3. The front end of the inner coiled body 13 is bonded to the front end of the small-diameter portion 2c of the core shaft 2 through the bulged portion 5. In addition, in a portion between the front end of the inner coiled body 13 and the proximal end of the coiled body 3, the proximal end of the inner coiled body 13 is bonded to the middle portion of the small-diameter portion 2c of the core shaft 2 and the middle portion of the coiled body 3 with the middle bonding portion 7. With this configuration, the tensile load and compressive load applied to the bulged portion 5 and the bonding portion 6 can be distributed among the core shaft 2, the coiled body 3, and the inner coiled body 13. Therefore, it is possible to prevent the bulged portion 5 and the bonding portion 6 from coming off from the small-diameter portion 2c of the core shaft 2. It is thus possible to further reliably prevent the coiled body 3 from coming off from the core shaft 2. As a result, the safety of the guidewire 21 can be further improved.

The inner coiled body 13 may be made of the same material as the coiled body 3 described in the first embodiment. The inner coiled body 13 may be a single-strand coil formed of one coil strand. However, the inner coiled body 13 is preferably a multiple-strand coiled body formed of a plurality of coil strands. The inner coiled body 13 as the multiple-strand coiled body has an increased strength. Therefore, it is possible to reliably prevent the bulged portion 5 and the bonding portion 6 from coming off from the core shaft 2 even when the large tensile load and compressive load are applied to the bulged portion 5 and the bonding portion 6. It is thus possible to reliably prevent the coiled body 3 from coming off from the core shaft 2. As a result, the safety of the guidewire 21 can be significantly improved.

Note that a gap is provided between the coil strands constituting the front end and the proximal end of the inner coiled body 13 so that an adhesive easily enters the coil. The gap between the coil strands constituting the multiple-strand coiled body can be formed by, for example, polishing the front end of the multiple-strand coiled body by means of electrolytic polishing.

The portion of the core shaft 2 bonded to the proximal end of the inner coiled body 13 may be positioned anywhere between the front end of the inner coiled body 13 and the proximal end of the coiled body 3. As illustrated in FIG. 3, it is preferable that the proximal end of the inner coiled body 13 be integrally bonded to the coiled body 3 and the core shaft 2. With this configuration, the bonding strength at the proximal end of the inner coiled body 13 can be increased. Therefore, the core shaft 2, the coiled body 3, the bulged portion 5 fixed to the inner coiled body 13, and the bonding portion 6, which are on the front side of the bonding portion of the proximal end of the inner coiled body 13, can be prevented from coming off from the members to which these portions are bonded. It is thus possible to further reliably prevent the coiled body 3 from coming off from the core shaft 2. As a result, the safety of the guidewire 21 can be further improved.

The guidewire 21 according to the present embodiment can be manufactured in the following manner.

The inner coiled body 13 is inserted into the front end of the small-diameter portion 2c of the core shaft 2. Flux is applied in advance to the small-diameter portion 2c of the core shaft 2 where the bulged portion 5 or the middle bonding portion 7 is to be formed, and the inner coiled body 13. Then, the proximal end of the inner coiled body 13 is temporarily bonded to the middle portion of the small-diameter portion 2c of the core shaft 2. The bulged portion 5 is formed by bringing, with a soldering iron, the first metal solder into contact with the tip portion of the small-diameter portion 2c of the core shaft 2 and the tip portion of the inner coiled body 13. As a result, the tip portion of the small-diameter portion 2c of the core shaft 2 is bonded to the tip portion of the inner coiled body 13.

Next, the front end, to which the inner coiled body 13 is bonded, of the small-diameter portion 2c of the core shaft 2 is inserted into the proximal side of the coiled body 3. Flux is applied to the proximal end of the outer coiled body 3 and the front end of the large-diameter portion 2a of the core shaft 2. After that, the proximal end of the outer coiled body 3 is bonded to the front end of the large-diameter portion 2a of the core shaft 2 with the proximal end bonding portion 9.

Next, flux is applied to the middle portion of the coiled body 3 where the middle bonding portion 7 is to be formed. Then, the portion to which the flux has been applied is bonded, with the middle bonding portion 7, to the portion at which the proximal end of the inner coiled body 13 has temporarily been bonded to the middle portion of the small-diameter portion 2c of the core shaft 2.

Finally, flux is applied to the front end of the small-diameter portion 2c of the core shaft 2 where the inner coiled body 13 and the bulged portion 5 are formed, and the front end of the coiled body 3. After that, the front end of the small-diameter portion 2c of the core shaft 2, the front end of the inner coiled body 13, and the front end of the coiled body 3 are bonded to one another using the soldering iron so that the second metal solder encloses the bulged portion 5. As a result, the bonding portion 6 is formed. With the above steps, the guidewire 21 is manufactured.

Note that, in the present embodiment, the outer diameter of the bulged portion 5 may be larger than the inner diameter of the coiled body 3. In this case, the bulged portion 5 smaller than the inner diameter of the coiled body 3 is formed. Then, the core shaft 2 is inserted into the coiled body 3. The small bulged portion 5 is exposed by shifting the coiled body 3 toward the proximal side thereof. After that, the first metal solder is added to the bulged portion 5. In this manner, the bulged portion 5 larger than the inner diameter of the coiled body 3 can be formed.

In FIG. 3, the front end of the small-diameter portion 2c of the core shaft 2, the front end of the inner coiled body 13, and the front end of the coiled body 3 are arranged in this order from the front end toward the proximal end of the guidewire 21. More specifically, among these three front ends, the front end of the small-diameter portion 2c of the core shaft 2 is the most distal portion, on the proximal side of which the front end of the inner coiled body 13 is arranged, and the front end of the coiled body 3 is at a further proximal side (the front end of the coiled body 3 is at the most proximal side). However, the arranging order of the front ends is not limited to the above example. The positional relationship among the front end of the small-diameter portion 2c of the core shaft 2, the front end of the inner coiled body 13, and the front end of the coiled body 3 may be different from that illustrated in FIG. 3, as long as the front end of the small-diameter portion 2c of the core shaft 2 is bonded to the front end of the inner coiled body 13 with the bulged portion 5, and the front end of the coiled body 3 is bonded to the front end of the core shaft 2 and the front end of the inner coiled body 13 with the bonding portion 6 so that the bonding portion 6 encloses the bulged portion 5.

Next, a guidewire 31 according to a fourth embodiment will be described with reference to FIGS. 4A and 4B, mainly focusing on the difference from the guidewire 1. In FIGS. 4A and 4B, the same portions as those of the guidewire 1 are denoted with the same reference symbols.

For easy understanding, FIG. 4A illustrates the entire guidewire 31 schematically with its length reduced. Therefore, the dimensional ratio of the entire guidewire illustrated is different from the dimensional ratio of the actual guidewire.

FIG. 4B is an enlarged view of the front end, enclosed in the circle A, of the guidewire 31 illustrated in FIG. 4A.

As illustrated in FIGS. 4A and 4B, in the guidewire 31, a concavo-convex engaging portion 4 is formed at the tip portion of a small-diameter portion 2c of a core shaft 2 (portion from the front end toward the proximal end of the small-diameter portion 2c). The guidewire 31 has the same configuration as the guidewire 1 except this engaging portion.

In the guidewire 31 described above, the concavo-convex engaging portion 4 is formed at the tip portion of the small-diameter portion 2c of the core shaft 2. At least one of a bulged portion 5 and a bonding portion 6 is positioned on the engaging portion 4. Therefore, the bonding strength between the front end of the small-diameter portion 2c of the core shaft 2 and the front end of a coiled body 3 can be significantly improved. It is thus possible to further reliably prevent the coiled body 3 from coming off from the core shaft 2. As a result, the safety of the guidewire 31 can be significantly improved.

The concavo-convex engaging portion 4 can be formed by grinding the core shaft 2 by means of, for example, blast or a Leutor. In this case, the concavo-convex engaging portion 4 is made of the same material as the core shaft 2.

More preferably, as illustrated in FIGS. 4A and 4B, a new concavo-convex engaging portion 4 made of the same or different material as/from the core shaft 2 is formed at the tip portion of the small-diameter portion 2c of the core shaft 2 by means of, for example, thermal spraying or vapor deposition. The new concavo-convex engaging portion 4 can thus be formed at the small-diameter portion 2c of the core shaft 2. As a result, the strength of the small-diameter portion 2c of the core shaft 2 can also be increased. This in turn makes it possible to further increase the bonding strength between the front end of the small-diameter portion 2c of the core shaft 2 and the front end of the coiled body 3.

Examples of the material for the concavo-convex engaging portion 4, which is formed at the tip portion of the small-diameter portion 2c of the core shaft 2 by, for example, thermal spraying or vapor deposition, include the material constituting the core shaft 2, titanium alloy, alumina, and ceramics such as hydroxyapatite.

As described above, in the guidewire 31, the concavo-convex engaging portion 4 is formed at the tip portion of the small-diameter portion 2c of the core shaft 2. At least one of the bulged portion 5 and the bonding portion 6 is positioned on the engaging portion 4. The front end of the small-diameter portion 2c of the core shaft 2 does not have to be positioned at the front end of the bulged portion 5 as long as the guidewire 31 has the configuration described above. As illustrated in FIGS. 4A and 4B, the tip portion of the small-diameter portion 2c of the core shaft 2 having the concavo-convex engaging portion 4 is preferably at the front side of the front end of the bulged portion 5. With this configuration, the bonding strength between the tip portion of the small-diameter portion 2c of the core shaft 2, and the bulged portion 5 and the bonding portion 6 can be increased.

The concavo-convex engaging portion 4 may be formed anywhere at the tip portion of the small-diameter portion 2c of the core shaft 2. As illustrated in FIGS. 4A and 4B, the concavo-convex engaging portion 4 preferably extends from the front end of the small-diameter portion 2c of the core shaft 2 toward the proximal end thereof. In this case, the bonding strength between the front end of the small-diameter portion 2c of the core shaft 2, and the bulged portion 5 and/or the bonding portion 6 can be increased.

The proximal end of the concavo-convex engaging portion 4 may be anywhere at the tip portion of the small-diameter portion 2c of the core shaft 2. As illustrated in FIGS. 4A and 4B, the proximal end of the concavo-convex engaging portion 4 is preferably on the proximal side of the proximal end of the bonding portion 6. In this case, the bonding strength between the tip portion of the small-diameter portion 2c of the core shaft 2 and the bonding portion 6 can be increased.

Next, a guidewire 41 according to a fifth embodiment will be described with reference to FIGS. 5A to 5E, mainly focusing on the difference from the guidewire 1. In FIGS. 5A to 5E, the same portions as those of the guidewire 1 are denoted with the same reference symbols.

Figure 5A:
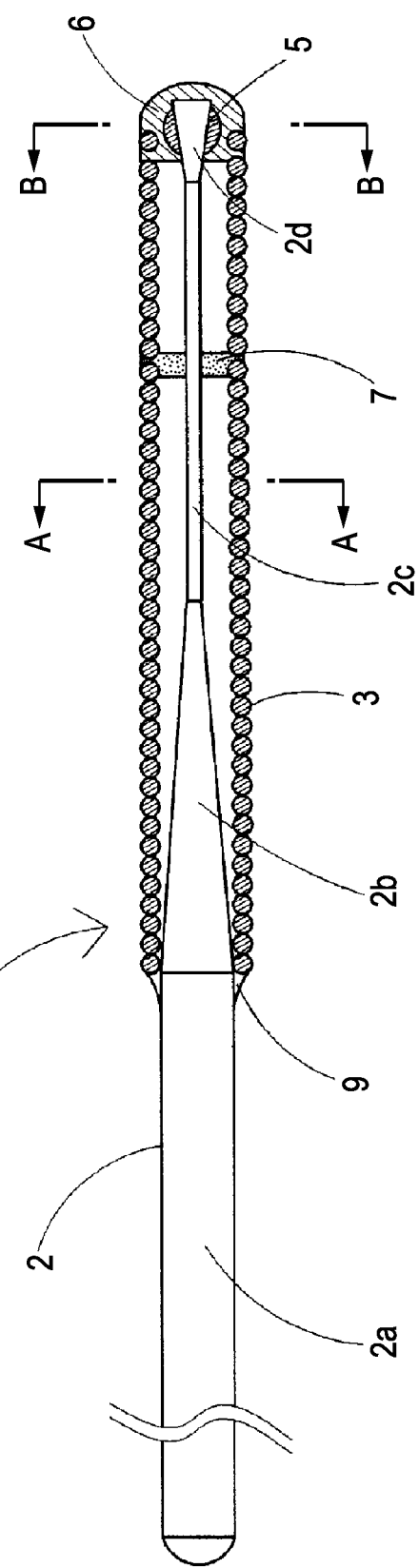

For easy understanding, FIG. 5A illustrates the entire guidewire 41 schematically with its length reduced. Therefore, the dimensional ratio of the entire guidewire illustrated is different from the dimensional ratio of the actual guidewire.

Figure 5E:
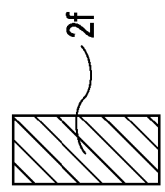
Figure 5D:
Figure 5C:
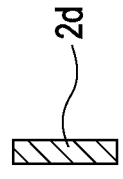
Figure 5B:

FIG. 5B is an enlarged view of the A-A section in FIG. 5A. FIG. 5C is an enlarged view of the B-B section in FIG. 5A. FIGS. 5D and 5E are enlarged views of the B-B section in FIG. 5A according to modifications.

In FIGS. 5A, 5B, and 5C, a core shaft 2 of the guidewire 41 has a flattened portion 2d having a flattened cross-section and positioned at the front end of a small-diameter portion 2c of the core shaft 2. The guidewire 41 has the same configuration as the guidewire 1 except this flattened portion.

As illustrated in FIGS. 5A and 5B, the small-diameter portion 2c of the core shaft 2 has a circular cross-section. As illustrated in FIGS. 5A and 5C, the flattened portion 2d of the core shaft 2 has the flattened cross-section. Note that the width of the flattened portion 2d of the core shaft 2 increases toward the front end thereof. In addition, the thickness of the flattened portion 2d decreases toward the front end thereof. Furthermore, the small-diameter portion 2c of the core shaft 2 has the same cross-sectional area as the flattened portion 2d of the core shaft 2.

In the guidewire 41 with the above configuration, the flattened portion 2d having the flattened cross-section is provided at the tip portion of the small-diameter portion 2c of the core shaft 2. The width or thickness of the flattened portion 2d increases toward the front end thereof. In addition, the bulged portion 5 is formed at the flattened portion 2d. Therefore, the bonding strength between the front end of the small-diameter portion 2c of the core shaft 2 and the front end of the coiled body 3 can be significantly increased. It is thus possible to reliably prevent the coiled body 3 from coming off from the core shaft 2. As a result, the safety of the guidewire 41 can be significantly improved.

The flattened portion 2d of the core shaft 2 can be formed by forming the small-diameter portion 2c of the core shaft 2 and then rolling the tip portion of the small-diameter portion 2c of the core shaft 2 using, for example, a pressing machine.

The front end of the flattened portion 2d of the core shaft 2 may be arranged at the front end of or inside the bulged portion 5. As illustrated in FIG. 5A, the front end of the flattened portion 2d of the core shaft 2 is preferably positioned on the front side of the front end of the bulged portion 5. With this configuration, the bonding strength between the flattened portion 2d of the core shaft 2, and the bulged portion 5 and the bonding portion 6 can be increased.

The proximal end of the flattened portion 2d of the core shaft 2 may be positioned at the proximal end of the bulged portion 5 or inside the bonding portion 6. As illustrated in FIG. 5A, the proximal end of the flattened portion 2d of the core shaft 2 is preferably positioned on the proximal side of the proximal end of the bonding portion 6. With this configuration, the bonding strength between the flattened portion 2d of the core shaft 2, and the bulged portion 5 and the bonding portion 6 can be increased.

FIG. 5D illustrates a modification of the core shaft 2 according to the present embodiment. In the configuration illustrated in FIG. 5D, a front end large-diameter portion 2e is provided, instead of the flattened portion 2d, at the core shaft 2. The front end large-diameter portion 2e has a similar circular cross-section to the small-diameter portion 2c of the core shaft 2. In addition, the front end large-diameter portion 2e has a larger cross-sectional area than the small-diameter portion 2c of the core shaft 2.

The front end large-diameter portion 2e of the core shaft 2 can be formed in the following manner. That is, the front end large-diameter portion 2e can be formed by grinding, using a grinding machine such as a centerless grinding machine, a portion having the same outer diameter as the large-diameter portion 2a and positioned on the front side of the small-diameter portion 2c of the core shaft 2 such that this ground portion has a larger outer diameter than the small-diameter portion 2c of the core shaft 2.

FIG. 5E illustrates another modification of the core shaft 2 according to the present embodiment. In the configuration illustrated in FIG. 5E, a large flattened portion 2f is provided, instead of the flattened portion 2d, at the core shaft 2. The large flattened portion 2f has a flattened cross-section. The large flattened portion 2f has a larger cross-sectional area than the flattened portion 2d of the core shaft 2. The width of the large flattened portion 2f increases toward the front end thereof. The thickness of the large flattened portion 2f, on the other hand, decreases toward the front end thereof.

The large flattened portion 2f of the core shaft 2 can be formed by forming, and then rolling with the pressing machine, the front end large-diameter portion 2e of the core shaft 2 according to the modification described above. The front end large-diameter portion 2e may be formed such that the diameter thereof increases toward the front end thereof. Rolling the front end large-diameter portion 2e, having the diameter increasing toward the front end thereof, makes it possible to form the large flattened portion 2f with its thickness and width increasing toward the front end thereof.

Next, a guidewire 51 according to a sixth embodiment will be described with reference to FIGS. 6A and 6B, mainly focusing on the difference from the guidewire 1. In FIGS. 6A and 6B, the same portions as those of the guidewire 1 are denoted with the same reference symbols.

For easy understanding, FIG. 6A illustrates the entire guidewire 51 schematically with its length reduced. Therefore, the dimensional ratio of the entire guidewire illustrated is different from the dimensional ratio of the actual guidewire.

FIG. 6B is an enlarged view of the front end, enclosed in the circle A, of the guidewire 51 illustrated in FIG. 6A.

As illustrated in FIGS. 6A and 6B, the guidewire 51 is different from the guidewire 1 in that a bonding layer 8 is provided on the outer surface of a bulged portion 5.

In the guidewire 51 described above, the bonding layer 8 is provided on the outer surface of the bulged portion 5. With this configuration, the bonding strength between the bulged portion 5 and a bonding portion 6 can be increased. It is thus possible to reliably prevent a coiled body 3 from coming off from a core shaft 2. As a result, the safety of the guidewire 51 can be significantly improved.

An adhesive such as epoxy resin can be used as a material constituting the bonding layer 8 when the bulged portion 5 or the bonding portion 6, adhering to each other, contains a resin component. When the bulged portion 5 and the bonding portion 6 are made of metal, the bonding layer 8 can be formed by, for example, sputtering or plating. When the bonding portion 6 to which the bonding layer 8 adheres is formed of, for example, a metal solder, examples of the material for the bonding layer 8 subject to sputtering or plating include Au, Ag, Sn, Rh, and Pd. The bonding strength between the bulged portion 5 and the bonding portion 6 can be improved by forming the bonding layer 8 on the outer surface of the bulged portion 5 through sputtering or plating using the above material.

Alternatively, the material for the bonding layer 8 may be metal containing voids, ceramics, or resin. With the bonding layer 8 containing voids, the material for the bonding portion 6 infiltrates the voids in the bonding layer 8 during formation of the bonding portion 6. This results in an anchor effect. Therefore, the bonding strength between the bulged portion 5 and the bonding portion 6 can be increased.

The bonding layer 8 described above can also function as a buffer layer which makes it difficult for an external impact, applied to the bonding portion 6, to transfer to the bulged portion 5. The bonding layer 8 can also function as a protective layer for preventing the material for the bulged portion 5 and the material for the bonding portion 6 from being mixed with each other. As a result, the bonding strength between the bulged portion 5 and the bonding portion 6 can be secured.

In FIGS. 6A and 6B, the front end of the small-diameter portion 2c of the core shaft 2 is positioned at the front end of the bulged portion 5. However, the configuration is not limited to this example, as long as the bonding layer 8 covers the outer surface of the bulged portion 5. That is, the front end of the small-diameter portion 2c of the core shaft 2 may be on the front side of the front end of the bulged portion 5.

The present invention is not limited to the embodiments described above. The disclosed embodiments can be modified in a variety of forms by those skilled in the art within the technical idea of the present invention.

In the guidewire 21 according to the third embodiment illustrated in FIG. 3, for example, a middle bonding portion for bonding only the coiled body 3 and the inner coiled body 13 may be provided at a middle portion in the longitudinal direction of the inner coiled body 13. It is thus possible to further reliably prevent the bulged portion 5 and the bonding portion 6 from coming off from the small-diameter portion 2c of the core shaft 2.

In the guidewire 31 according to the fourth embodiment illustrated in FIGS. 4A and 4B, the concavo-convex engaging portion 4 is provided at the tip portion of the small-diameter portion 2c of the core shaft 2. The concavo-convex engaging portion 4 may also be provided in the coiled body 3 of the guidewire 1 according to the first embodiment illustrated in FIG. 1, or in the inner coiled body 13 of the guidewire 21 according to the third embodiment illustrated in FIG. 3.

While the foregoing embodiments have been shown and described in detail, the foregoing description is in all aspects illustrative and not restrictive. It is therefore understood that numerous modifications and variations can be devised without departing from the spirit and scope of the invention.

What is claimed is:

1. A guidewire comprising:
a core shaft;
a coiled body covering the core shaft;
a bulged portion formed separately on a tip portion of the core shaft, the bulged portion having a width that varies along the length of the bulged portion; and
a bonding portion by which a front end of the coiled body is bonded to a front end of the core shaft, the bonding portion enclosing the bulged portion and contacting the core shaft, wherein
a material constituting the bulged portion is a first metal solder, and
a material constituting the bonding portion is a second metal solder having a lower melting point than the first metal solder.

2. The guidewire according to claim 1,
wherein the material constituting the bulged portion has a higher stiffness than the material constituting the bonding portion.

3. The guidewire according to claim 1,
wherein the first metal solder contains 80 wt % or more gold component.

4. The guidewire according to claim 1,
wherein the bulged portion has an outer diameter larger than an inner diameter of the coiled body.

5. The guidewire according to claim 1, further comprising:
an inner coiled body positioned inside the coiled body,
wherein a front end of the inner coiled body is bonded to the core shaft through the bulged portion, and
a proximal end of the inner coiled body is bonded to the core shaft between the front end of the inner coiled body and a proximal end of the coiled body.

6. The guidewire according to claim 1,
wherein a concavo-convex engaging portion is provided at the tip portion of the core shaft, and
at least one of the bulged portion and the bonding portion is positioned on the concavo-convex engaging portion.

7. The guidewire according to claim 1,
wherein a flattened portion having a flattened cross-section is provided at the tip portion of the core shaft,
at least one of a width and a thickness of the flattened portion increases toward a front end thereof, and
the bulged portion is formed at the flattened portion.

8. The guidewire according to claim 1,
wherein at least one of the coiled body, the bulged portion, and the bonding portion is constituted, at least in part, of a radiopaque material.

* * * * *